(12) United States Patent
Beyerinck et al.

(10) Patent No.: US 8,828,443 B2
(45) Date of Patent: *Sep. 9, 2014

(54) METHOD FOR MAKING HOMOGENEOUS SPRAY-DRIED SOLID AMORPHOUS DRUG DISPERSIONS UTILIZING MODIFIED SPRAY-DRYING APPARATUS

(71) Applicant: Bend Research, Inc., Bend, OR (US)

(72) Inventors: Ronald A. Beyerinck, Bend, OR (US); Heather L. M. Diebele, Bend, OR (US); Dan E. Dobry, Bend, OR (US); Roderick J. Ray, Bend, OR (US); Dana M. Settell, Bend, OR (US); Ken R. Spence, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/727,391

(22) Filed: Dec. 26, 2012

(65) Prior Publication Data

US 2014/0017314 A1 Jan. 16, 2014

Related U.S. Application Data

(62) Division of application No. 13/165,732, filed on Jun. 21, 2011, now Pat. No. 8,343,550, which is a division of application No. 10/766,651, filed on Jan. 27, 2004, now abandoned, which is a division of application No. 10/353,746, filed on Jan. 28, 2003, now Pat. No. 6,763,607.

(60) Provisional application No. 60/354,080, filed on Feb. 1, 2002.

(51) Int. Cl.
*A61K 9/16* (2006.01)
*A61K 9/14* (2006.01)
*B29B 9/00* (2006.01)
*F26B 3/08* (2006.01)
*A61J 3/02* (2006.01)

(52) U.S. Cl.
CPC ............... *A61J 3/02* (2013.01); *A61K 9/1952* (2013.01); *A61K 9/146* (2013.01); *A61K 9/1694* (2013.01)
USPC .............. 424/489; 424/490; 264/5; 34/372

(58) Field of Classification Search
CPC ......... A61J 3/02; A61K 9/146; A61K 9/1652; A61K 9/1694; A61K 9/5078; F26B 3/12
USPC .................. 424/489, 490; 264/5; 34/372
See application file for complete search history.

(56) References Cited

U.S. PATENT DOCUMENTS 4,056,599 A 11/1977 Fox, III et al.
4,187,617 A 2/1980 Becker, Jr. et al.
(Continued)

FOREIGN PATENT DOCUMENTS

EP 0214441 A2 3/1987
EP 0436373 A1 7/1991
(Continued)

OTHER PUBLICATIONS

Material Safety Data Sheet (MSDS), "Acetone," Sciencelab.com, pp. 1-7, 2005.
(Continued)

*Primary Examiner* — Aradhana Sasan
(74) *Attorney, Agent, or Firm* — Klarquist Sparkman, LLP

(57) ABSTRACT

Conventional spray-drying methods are improved by incorporation of a pressure nozzle and a diffuser plate to improve the flow of drying gas and a drying chamber extension to increase drying time, such improvements leading to the formation of homogeneous solid dispersions of drugs in concentration-enhancing polymers.

8 Claims, 7 Drawing Sheets

(56) References Cited

U.S. PATENT DOCUMENTS

| | | | |
|---|---|---|---|
| 4,233,114 | A | 11/1980 | Gastaldi |
| 4,344,934 | A | 8/1982 | Martin et al. |
| 5,019,400 | A | 5/1991 | Gombotz et al. |
| 5,272,820 | A | 12/1993 | Ito et al. |
| 5,456,923 | A | 10/1995 | Nakamichi et al. |
| 5,919,408 | A | 7/1999 | Muller et al. |
| 5,958,458 | A | 9/1999 | Norling et al. |
| 6,020,403 | A | 2/2000 | Eck et al. |
| 6,068,859 | A | 5/2000 | Curatolo et al. |
| 6,121,283 | A | 9/2000 | Chang et al. |
| 6,194,000 | B1 | 2/2001 | Smith et al. |
| 6,197,348 | B1 | 3/2001 | Morella et al. |
| 6,253,463 | B1 | 7/2001 | Hansen |
| 6,350,786 | B1 | 2/2002 | Albano et al. |
| 6,651,898 | B2 | 11/2003 | Nowotny et al. |
| 6,711,831 | B1 | 3/2004 | Hansen et al. |
| 6,763,607 | B2 | 7/2004 | Beyerinck et al. |
| 6,848,197 | B2 | 2/2005 | Chen et al. |
| 6,973,741 | B2 | 12/2005 | Beyerinck et al. |
| 7,780,988 | B2 | 8/2010 | Beyerinck et al. |
| 8,343,550 | B2 * | 1/2013 | Beyerinck et al. ............ 424/490 |
| 2001/0053791 | A1 | 12/2001 | Babcock et al. |
| 2002/0103225 | A1 | 8/2002 | Curatolo et al. |
| 2003/0064108 | A1 | 4/2003 | Lukas et al. |
| 2003/0086976 | A1 | 5/2003 | Hayes et al. |
| 2003/0198674 | A1 | 10/2003 | Curatolo et al. |
| 2003/0225104 | A1 | 12/2003 | Hayes et al. |

FOREIGN PATENT DOCUMENTS

| | | |
|---|---|---|
| EP | 0492007 B1 | 2/1995 |
| EP | 0400910 B1 | 11/1995 |
| EP | 0901786 A2 | 3/1999 |
| EP | 1027886 A2 | 8/2000 |
| EP | 1027887 A2 | 8/2000 |
| EP | 1027888 A2 | 8/2000 |
| GB | 475635 | 11/1937 |
| GB | 1131242 | 10/1968 |
| GB | 1329791 | 9/1973 |
| GB | 2231266 A | 11/1990 |
| WO | 96/41632 A1 | 12/1996 |
| WO | 97/38678 A1 | 10/1997 |
| WO | 0064552 A1 | 11/2000 |
| WO | 0119796 A1 | 3/2001 |
| WO | 0168055 A1 | 9/2001 |
| WO | 0168092 A2 | 9/2001 |
| WO | 0168645 A2 | 9/2001 |
| WO | 03000226 A2 | 1/2003 |
| WO | 03063821 A2 | 8/2003 |
| WO | 03063832 A1 | 8/2003 |
| WO | 03063833 A1 | 8/2003 |
| WO | 03075836 A2 | 9/2003 |

OTHER PUBLICATIONS

Deis, Ronald, "Spray-Drying: Innovative Use of an Old Process," Design Elements, May 1997, pp. 1-7.

Marshall, W. R. Jr. et al., "Principles of Spray Drying: Part II—Elements of Spray-Dryer Design," Chemical Engineering Progress, 47:11, pp. 575-584, 1950.

Marshall, W. R. Jr., "Atomization and Spray Drying," American Institute of Chemical Engineers, New York, NY chapter VI, pp. 50-56, 1954.

Newton, J. M., "Spray Drying and Its Application in Pharmaceuticals," Manufacturing Chemist and Aerosol News, 37:4, pp. 33-36, 1966.

Shebler, K. J., "Variables in spray Drier Design and Operation," The Australian Journal of Dairy Technology, 23:3, pp. 131-136, 1970.

Author Unknown, "Milk powder build-up prevented in Japanese nozzle spray drier," Food Technology in New Zealand, p. 27, Sep. 1972.

Kutcher, P., "Future Trends in Spray Drying," Winter School on spray Drying: Papers and discussions from the Winter School/Conducted by Australian Society of Dairy Technology, pp. 75-81, 1975.

Gauvin, W. H. et al., "Basic Concepts of Spray Dryer Design," AIChE Journal, 22:4, pp. 713-724, 1976.

Keey, R. B. et al., "Behavior of Spray Dryers with Nozzle Atomizers," The Chemical engineer, Jul./Aug., pp. 516-521, 1976.

Keey, R. B. et al., "Residence-Time Distribution of Air in a Tall-Form Spray Chamber," Chemical Engineering Science, vol. 32, pp. 1219-1226, 1977.

Dittman, F. W., et al., "Establishing the parameters for a spray dryer," Chemical Engineering, 84:2, pp. 108-112, 1977.

Yates, W. E., et al., "Nozzle Orientation, Air Speed and Spray Formulation Affects on Drop Size Spectrums," Transactions of the ASAE, 26:6, pp. 1638-1643, 1983.

Crowe, C. T., "Droplet-Gas Interaction in Counter-Current Spray Dryers," Drying Technology, 1:1, pp. 35-56, 1983-1984.

Masters, K., Spray Drying Handbook, 4th ed., George Godwin, London, England, pp. 54-55, 1985.

Masters, K., "Spray-Air Contact (Mixing and Flow)," Spray Drying Handbook, 4th ed., George Godwin, London, England, chapter 7, pp. 263-269, 1985.

Usui, H., et al. "Residence-Time Distribution of Air Flow in a Spray Drying Chamber," Journal of Chemical Engineering of Japan, 18:5, pp. 464-466, 1985.

Hayashi, H., et al., "Spray Drying Characteristics by a Centrifugal Pressure Nozzle With Large Orifice Diameter," Drying Technology, 4:3, pp. 331-342, 1986.

Zhelev, J. B., " Experimental Investigation of Flow Pattern in a Spray-Dryer," Drying Technology, 7:3, pp. 477-485, 1989.

Lefebvre, A. H., Atomization and Sprays, Taylor and Francis Publishers, chapter 4, pp. 105-153, 1989.

Lefebvre, A. H., Atomization and Sprays, Taylor and Francis Publishers, chapter 9, pp. 367-409, 1989.

Ferrazza, G., et al., "The Right Spray Demands the Right Nozzle," Chemical Engineering, pp. 177-184, Nov. 1990.

Masters, K., Drying 91, A.S. Mujumdar and I Filkova (eds), elsevier Science Publishers, Amsterdam, The Netherlands, pp. 56-73, 1991.

Oakley, D. E., et al., "Spray/Gas Mixing Behaviour Within Spray Dryers," Drying 91, A.S. Mujumdar and I Filkova (eds), Elsevier Science Publishers, Amsterdam, The Netherlands, pp. 303-313, 1991.

Liang, G. et al, "Factors Influencing Flow Patterns, Temperature Fields and Consequent Drying Rates in Spray Drying," Drying technology, 9:1, pp. 1-25, 1991.

Killeen, J.J., "The Process of Spray Drying and Spray Congealing," Pharmaceutical Engineering, pp. 56-62, Jul./Aug. 1991.

P. Giunchedi, et al., "Cellulose acetate butyrate and polycaprolactone for ketoprofen spray-dried microsphere preparation," Journal of Microencapsulation, 11;4, pp. 381-393, 1994.

U. Conte, et al., "Spray Dried Polylactide Microsphere Preparation: Influence of the Technological Parameters," Drug Development and Industrial Pharmacy, 20:3, pp. 235-258, 1994.

P. Giunchedi, et al., "Spray-drying as a preparation method of microparticulate drug delivery sytems: an overview," S. T. P. Pharma Sciences, 5:4, pp. 276-290, 1995.

C. Bitz, et al., "Influence of the preparation method on residual solvents in biodegradable microspheres," International Journal of Pharmaceutics, vol. 131, pp. 171-181, 1996.

Oakley, D.E., "Produce Uniform Particles by Spray Drying," Chemical Engineering Progress, pp. 48-54, Oct. 1997.

S. Wendel et al., Pharmaceutical Technology, pp. 124-156, Oct. 1997.

B. Ertl, et al., "Influence of manufacturing parameters on the size characteristics and the release profile of ketoprofen from spray dried poly (d,l-lactic-co-glycolic acid) microspheres," Scientia Pharmaceutica, vol. 66, pp. 105-115, 1998.

A. Billon, et al., "Effects of Cellulose Derivatives and Additives in the Spray-Drying Preparation of Acetaminophen Delivery Systems," Drug Development and Industrial Pharmacy, 25;11, pp. 1149-1156, 1999.

B. Baras, et al., "Parameters influencing the antigen release from spray-dried poly (DL-lactide) microparticles," International Journal of Pharmaceutics, vol. 200, pp. 133-145, 2000.

(56) References Cited

OTHER PUBLICATIONS

E. Esposito, et al., "Production of Eudragit Microparticles by Spray-Drying Technique: Influence of Experimental Parameters on Morphological and Dimensional Characteristics," Pharmaceutical Development and Technology, 5:2, pp. 267-278, 2000.

T. Hino, et al., "Development of a new type nozzle and spray-drier for industrial production of fine powders," European Journal of Pharmaceutics and Biopharmaceutics, vol. 49, pp. 79-85, 2000.

H. Liu, Science and Engineering of Droplets—Fundamentals and Applications, Noyes publications, Park Ridge, NJ, pp. 19-65, 2000.

Y.-J. Fu, et al., "Characteristic and controlled release of anticancer drug loaded poly (D,L-lactide) microparticles prepared by spray drying technique," Journal of Microencapsulation, 18:6, pp. 733-747, 2001.

* cited by examiner

METHOD FOR MAKING HOMOGENEOUS SPRAY-DRIED SOLID AMORPHOUS DRUG DISPERSIONS UTILIZING MODIFIED SPRAY-DRYING APPARATUS

This is a divisional of U.S. application Ser. No. 13/165,732 filed Jun. 21, 2011, now U.S. Pat. No. 8,343,550, which is a divisional of U.S. application Ser. No. 10/766,651, filed Jan. 27, 2004, which is a divisional of U.S. application Ser. No. 10/353,746, filed Jan. 28, 2003, now U.S. Pat. No. 6,763,607, which is a nonprovisional of U.S. Application No. 60/354,080, filed Feb. 1, 2002, the priority of all of which is claimed pursuant to 35 USC §120.

BACKGROUND OF THE INVENTION

The use of spray-drying to produce powders from fluid feed stocks is well known, with applications ranging from powdered milk to bulk chemicals and pharmaceuticals. See U.S. Pat. No. 4,187,617 and Mujumbar et al., *Drying 91*, pages 56-73 (1991). The use of spray-drying to form solid amorphous dispersions of drugs and concentration-enhancing polymers is also known. See commonly owned European Patent Applications Nos. 0 901 786, 1 027 886, 1 027 887, 1 027 888, and commonly-owned PCT Applications Nos. WO 00/168092 and WO 00/168055. And the use of a perforated plate as an air disperser for a spray-dryer using a nozzle atomizer is also known. See Masters, *Spray Drying Handbook*, pages 263-268 (4$^{th}$ ed 1985).

A typical spray-drying apparatus comprises a drying chamber, atomizing means for atomizing a solvent-containing feed into the drying chamber, a source of heated drying gas that flows into the drying chamber to remove solvent from the atomized solvent-containing feed and product collection means located downstream of the drying chamber. Examples of such apparatus include Niro Models PSD-1, PSD-2 and PSD-4 (Niro A/S, Soeborg, Denmark). When used for forming solid amorphous dispersions by spray-drying, conventional wisdom suggests that to achieve rapid removal of solvent required to form a homogeneous solid amorphous dispersion, the droplets of atomized solvent-containing feed should be small. The prior art therefore uses spray-drying apparatus equipped with a two-fluid nozzle for atomizing the solvent-containing feed. Such nozzles produce small droplets of feed solution, typically 5 to 30 µm in diameter, and turbulent mixing of the liquid feed droplets and drying gas, leading to rapid drying of the fluid to form solid particles. When used in the prescribed manner, such spray-drying apparatus are effective in forming substantially amorphous and substantially homogeneous solid-amorphous dispersions of drug and polymer that show concentration enhancement when introduced to an environment of use. However, as noted above, the spray-dried particles produced in such apparatus often have small median particle sizes (less than about 30 µm in diameter) and a large amount of "fines" (particles with diameters of less than about 10 µm). The product also typically has a high specific volume. Specific volume is the volume of the spray-dried powder divided by its mass—typically reported in units of cm$^3$/g. Generally, the higher the specific volume of a powder, the poorer its flow characteristics. As a result, the dispersions produced using a spray-drying apparatus equipped with a two-fluid nozzle have relatively poor flow characteristics and poor collection efficiency.

The inventors have found that the flow characteristics and collection efficiency of spray-dried dispersions can be improved by using a spray-drying apparatus equipped with atomizing means that produces droplets with an average droplet diameter of 50 µm or larger, with less than about 10 vol % of the droplets having a size less than 10 µm. Such an atomizing means is referred to herein as a "pressure nozzle." It has been discovered that homogeneous solid amorphous dispersions formed using pressure nozzles have relatively larger median particle sizes, with minimal fines present. The resulting dispersions therefore have improved flow characteristics and improved collection efficiencies. See commonly owned U.S. Provisional Application No. 60/353,986 filed Feb. 1, 2002 and incorporated herein by reference.

However, all else being equal, the rate of removal of solvent from such larger droplets produced by a pressure nozzle is slower than that from smaller droplets, such as those produced by a two-fluid nozzle. Conventionally, to counteract this tendency for large droplets to dry more slowly, drying gas is introduced in a flow direction that is not parallel to the atomized droplet flow. Drying gas introduced in this manner induces large circulation cells that carry droplets or particles initially directed downward back up to the top of the dryer. Such flow causes turbulent mixing of the drying gas and atomized spray solution, leading to more rapid drying of the droplets. However, these conventional methods for spray-drying large particles-result in (1) build-up of material on the nozzle itself, as well as on the dryer surface near the drying gas inlet, (2) excessively rapid drying of some of the particles, and (3) less uniform drying conditions. As a result, the product produced tends to have poor content uniformity, high specific volumes, poor flow characteristics, and when the build-up occurs on hot surfaces, the potential for chemical degradation of the product. Thus, such non-parallel introduction of drying gas to a conventional spray-drying apparatus should be avoided.

There is therefore a need in the art for an improved spray-drying process that results in the production of solid amorphous dispersions at high yield with improved flow characteristics, improved content uniformity, and improved collection efficiency.

BRIEF SUMMARY OF THE INVENTION

According to the present invention there is provided an improved method for making homogeneous spray-dried solid amorphous dispersions of pharmaceuticals in a concentration-enhancing polymer, the improved method including the use of a gas-dispersing means that facilitates organized plug flow of the drying gas, a drying chamber having a particular height and volume and an atomizing means that produces droplets with a median droplet diameter of 50 µm or larger, with less than about 10 vol % of the droplets having a size less than 10 µm, referred to herein as a pressure nozzle.

DETAILED DESCRIPTION OF THE INVENTION

Figure 1:
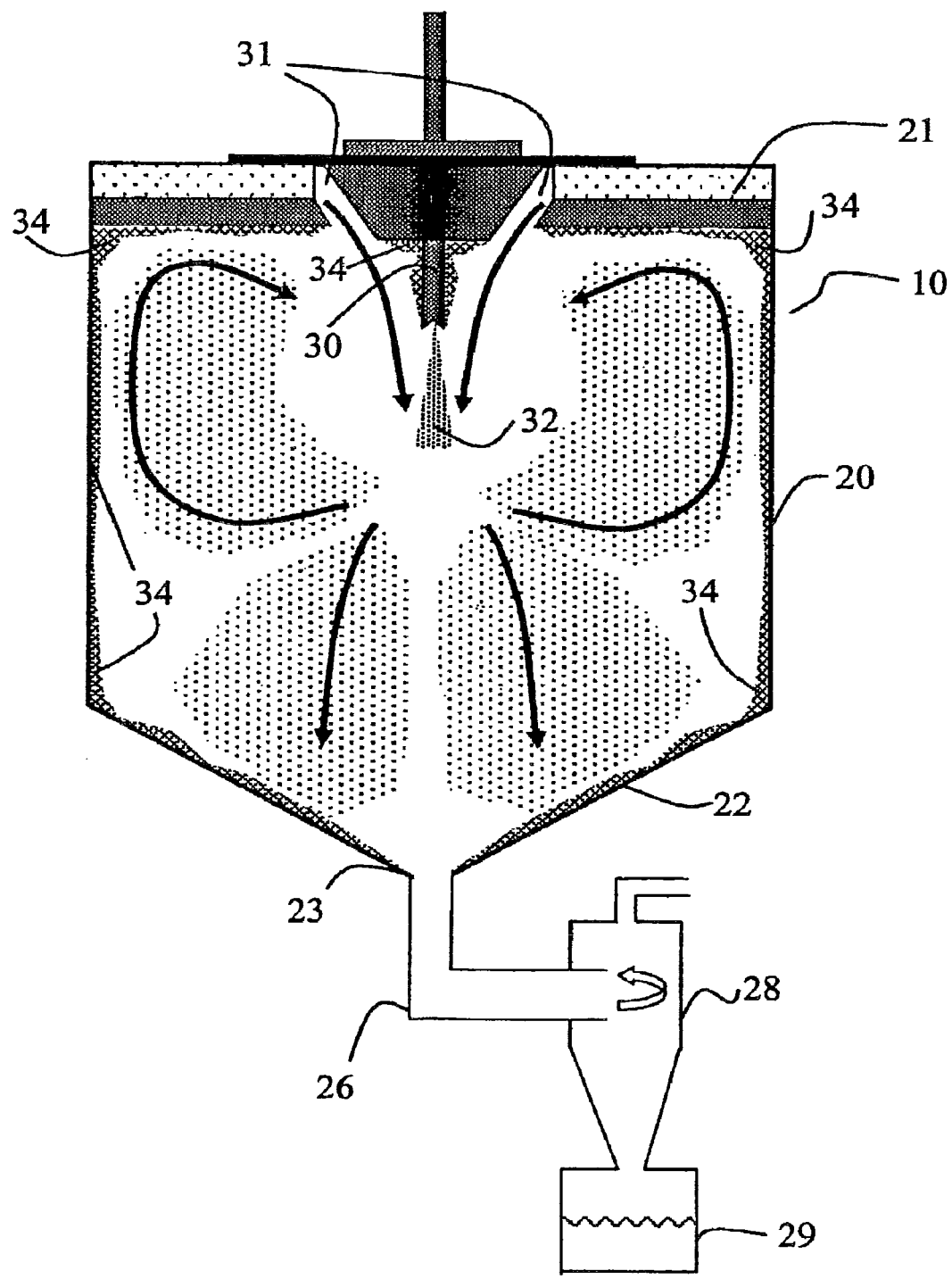
FIG. 1 is a cross-sectional schematic of a spray-drying apparatus equipped with a conventional non-parallel introduction of drying gas to promote rapid mixing of the drying gas and atomized solvent-containing feed.

Turning to the drawings, wherein the same numerals refer to like elements, there is shown in FIG. 1 a typical prior art spray-drying apparatus 10. In the following discussion it is assumed that the spray-drying apparatus is cylindrical. However, the dryer may take any other shape suitable for spray drying a solvent-bearing feed, including square, rectangular, and octagonal. The spray-drying apparatus is also depicted as having one atomizing means. However, multiple atomizing means can be included in the spray-drying apparatus to achieve higher throughput of the solvent-bearing feed.

The apparatus shown in FIG. 1 comprises a drying chamber 20, a drying chamber top 21, a collection cone 22, a connecting duct 26 connected to the distal end 23 of the collection cone, a cyclone 28 and a collection vessel 29. An atomizer 30 is shown atomizing a solvent-bearing feed 32. Drying gas from a drying gas source (not shown) is introduced through drying gas inlets 31, typically via an annular opening in drying chamber top 21, in a flow direction that is not parallel to the atomized droplet flow which is typically introduced vertically at the center of the top of the dryer via atomizing means 30. The non-parallel drying gas flow typically has an inward vector that is toward the atomized droplets near the center of the chamber and a radial vector that is an off-center flow. Drying gas introduced in this manner induces large scale flow that is circular (generally parallel to the circumference of the cylindrical chamber), and that creates large circulation cells that carry droplets or particles initially downward and then back up to the drying chamber top 21 so as to cause a large fraction to pass near drying gas inlet 31 and atomizing means 30, as indicated by the arrows in FIG. 1. Such flow introduces rapid and turbulent mixing of the drying gas and atomized solvent-bearing feed 32, leading to rapid drying of the droplets to form the solid particles of the dispersion. The solid dispersion particles are entrained by the drying gas through collection cone 22 to connecting duct 26, and then to cyclone 28. In the cyclone, the particles are separated from the drying gas and evaporated solvent, allowing the particles to be collected in collection vessel 29. Instead of a cyclone, a filter can be used to separate and collect the particles from the drying gas and evaporated solvent.

The drying gas may be virtually any gas, but to minimize the risk of fire or explosions due to ignition of flammable vapors, and to minimize undesirable oxidation of the drug, concentration-enhancing polymer, or other materials in the dispersion, an inert gas such as nitrogen, nitrogen-enriched air, or argon is utilized. The temperature of the drying gas at the gas inlet of apparatus 10 is typically from about 60° to about 300° C. The temperature of the product particles, drying gas, and evaporated solvent at the outlet or distal end 23 of collection cone 22 typically ranges from about 0° C. to about 100° C.

Figure 3:
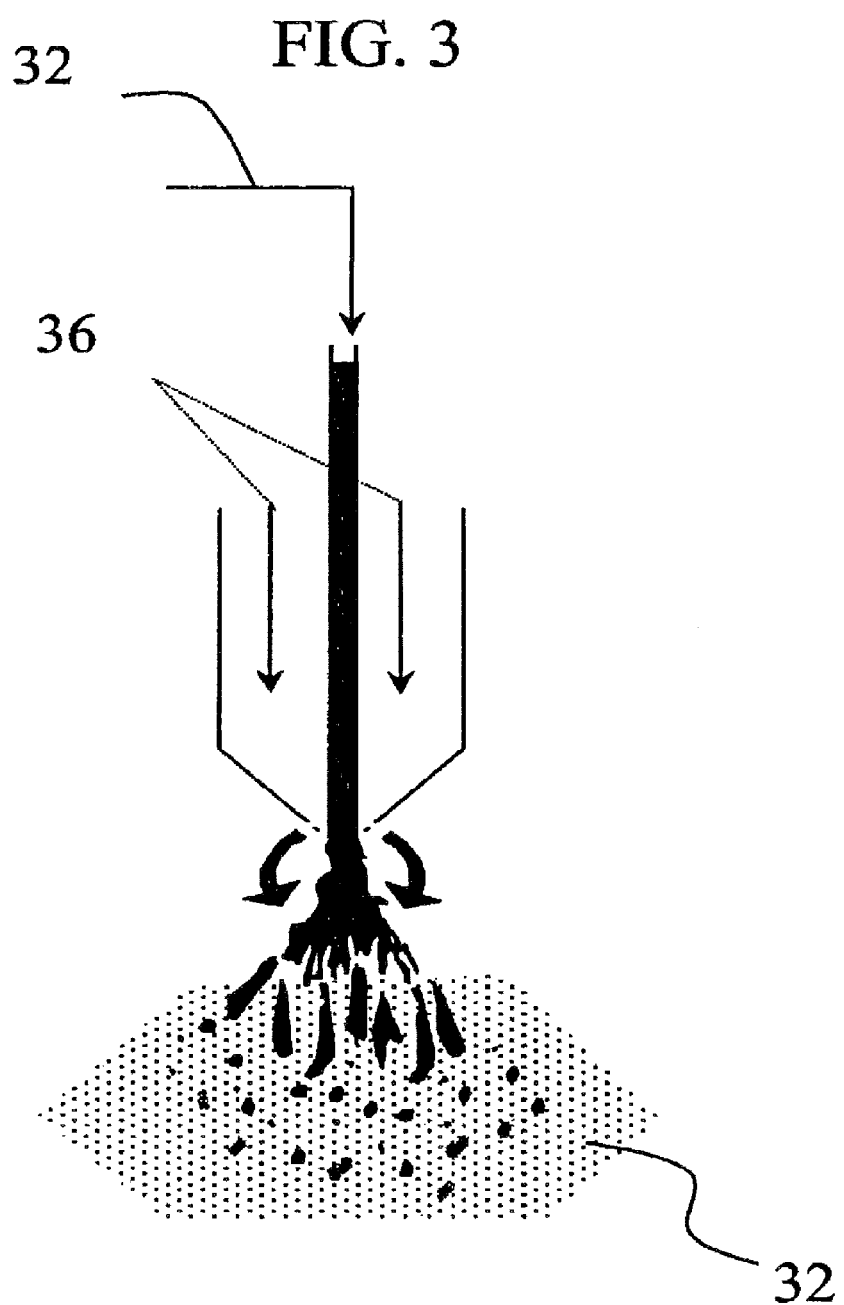
FIG. 3 is a schematic of a typical two-fluid spray nozzle.

As noted above, conventional wisdom is that the formation of a homogeneous solid amorphous dispersion of a low-solubility drug and a concentration-enhancing polymer requires rapid solidification of the atomized droplets. To accomplish this, the prior art has used an apparatus such as that shown in FIG. 1 equipped with atomizing means such as the two-fluid nozzle shown in FIG. 3, that produces relatively small droplets, generally with median diameters of 50 µm or less, and typical average droplet diameters of 5 to 30 µm. In such two-fluid nozzles, the solvent-containing feed 32 is mixed with an atomizing gas 36, such as air or nitrogen, atomizing the feed into small droplets. This small droplet size, along with the turbulent mixing of a portion of the drying gas within the nozzle as well as at the outlet of the nozzle, results in a large surface area and driving force for evaporation of the solvent from the droplet, leading to rapid removal of solvent from the droplet. The resulting dispersion particles typically have median diameters of 30 µm or less. In addition, a large proportion, typically greater than about 10 vol % of the particles, constitute fines having diameters of less than 10 µm, which leads to relatively poor flow characteristics for the dispersion particles. These fines not only generally lead to poor flow characteristics for the product, but are sufficiently small that the static electrical charge they often incur is large relative to their mass due to their large surface-to-mass ratio. As a result, they have poor collection efficiencies in cyclone-based and filter-based collections schemes.

The inventors have discovered that spray-dried dispersions with improved properties can be obtained by using a pressure nozzle, that is, atomizing means that produces droplets with a median droplet diameter of 50 µm or larger, with less than about 10 vol % of the droplets having a size less than 10 µm. The droplets produced by such atomizing means are significantly larger than those used in conventional spray-drying apparatus, such as those equipped with a two-fluid nozzle. As a result, the rate of removal of solvent from such larger droplets is slower than that from smaller droplets. Despite this slower rate of solvent removal, the inventors have discovered that homogeneous spray-dried dispersions can be formed using such atomizing means.

When a pressure nozzle is used in a conventional spray-dryer apparatus such as that shown in FIG. 1, the resulting non-parallel flow creates large circulation cells as described above that causes rapid and turbulent mixing of the drying gas and atomized spray solution, leading to rapid drying of the larger droplets. This approach has the benefit of allowing the larger droplets formed by pressure nozzles to be dried in a conventional-sized drying chamber. As a result, homogeneous solid amorphous dispersions may be successfully made in this manner. However, the resulting rapid drying of the particles nevertheless can lead to high specific volume product with relatively poor flow characteristics. In addition, the drying conditions for the droplets are not uniform, resulting in a product that has a wide range of particle sizes, densities, and morphologies. Finally, as explained below, in such an apparatus there is a build-up of material therein that reduces yield and can lead to frequent shutdowns of the apparatus.

Figure 2:
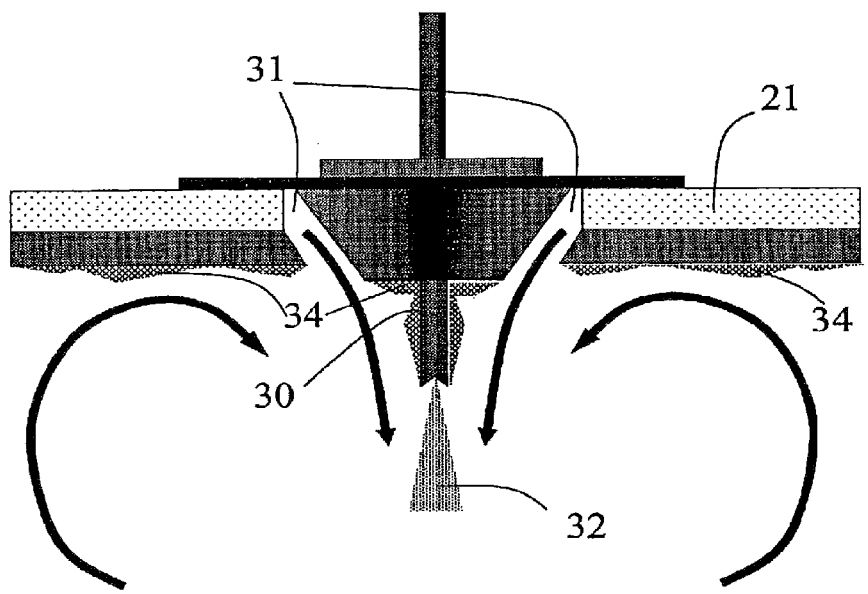
FIG. 2 is a cross-sectional schematic of a portion of the apparatus shown in FIG. 1 depicting product build-up around the atomizer.

A principal drawback of the prior art apparatus of FIG. 1, especially when equipped with a pressure nozzle atomizer, is the build-up of material 34 on the inside of drying chamber top 21 near the drying gas inlets 31 and on and around spray nozzle 30. This build-up of material 34 is believed to be due in part to the circulation cells that carry droplets or partially dried particles up to chamber top 21 and past drying gas inlet 31 and atomizing means 30 as noted above and as illustrated by the arrows in FIG. 1. This causes droplets of the solvent-bearing feed 32 as well as partially dried particles to contact the hot surfaces of drying chamber top 21 and atomizing means 30 before they are fully dry. The accumulation of material 34 on and around the atomizer 30 depicted in FIG. 2 eventually impedes the flow of solvent-bearing feed 32, which in turn adversely alters the atomization of the feed, resulting in changes in droplet size and diminishing the flow of feed, thereby reducing the capacity of the spray-drying apparatus. This requires frequent shutdown and cleaning of the apparatus to maintain high product quality and productivity.

The inventors have made the surprising discovery that by introducing the drying gas so that its primary axis of flow is generally parallel to the axis of atomizing means 30 and so that it flows relatively uniformly across the diameter of drying chamber 20, even though flow within the drying chamber is locally turbulent, a generally downward "organized plug flow" (described below) may be maintained for a significant distance away from chamber top 21. Introducing the drying gas in this manner (1) prevents circulation of particles upwardly back up to chamber top 21; (2) avoids build-up material 34 on atomizing means 30, chamber top 21, and drying gas inlets 31; (3) provides more uniform drying conditions for the droplets, leading to more uniform product; and (4) allows slower drying of the droplets, which generally allows for a denser, lower specific volume product to be formed that has improved flow characteristics.

Figure 4:
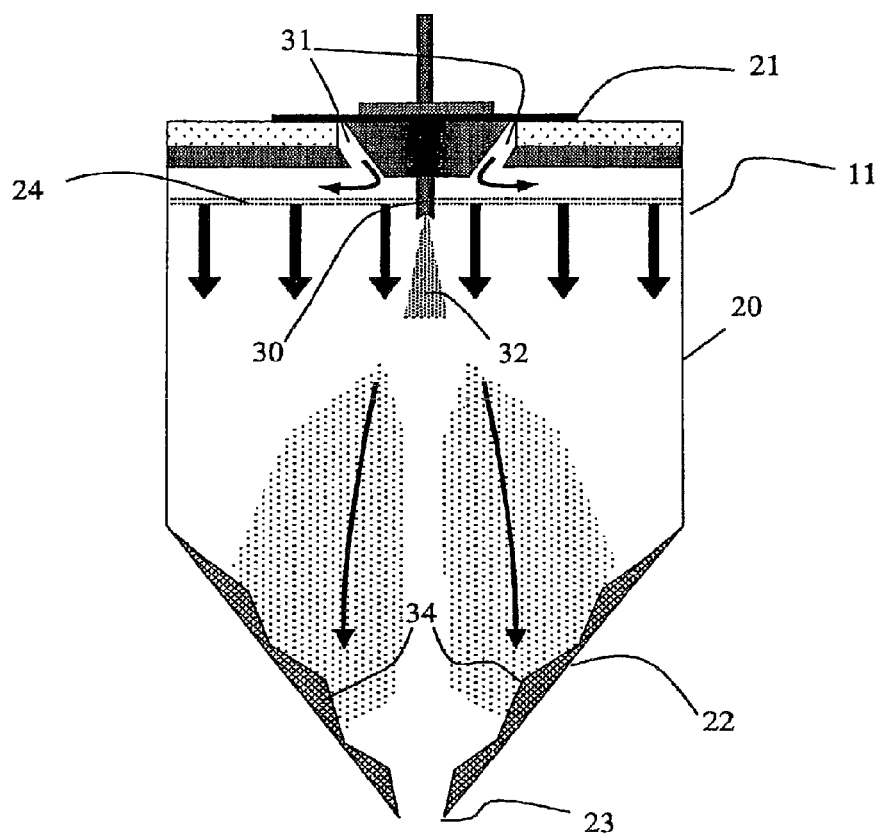
FIG. 4 is a cross-sectional schematic of the apparatus shown in FIG. 1 with a gas-dispersing means to provide organized plug flow of the drying gas.

There is shown in FIG. 4 a cross-sectional schematic of a modified spray-drying apparatus 11 without any product collection means, which includes gas-dispersing means 24 situated within drying chamber 20 and below drying chamber top 21. Gas-dispersing means 24 allows drying gas to be introduced into chamber 20 so that it is initially generally parallel to the axis of atomizing means 30 and is distributed relatively evenly across the diameter of the apparatus, shown schematically by the multiple downwardly pointing arrows in the upper portion of FIG. 4. The drying gas is thus introduced so that its flow through the upper portion of the spray-dryer can be described as "organized plug flow" away from the top of the apparatus. By "organized plug flow" is meant that the flow of drying gas satisfies at least one of the following two conditions. First, the drying gas velocity vector parallel to the walls of drying chamber 20, at any point across the diameter of the drying chamber, is predominantly towards the distal end 23 of collection cone 22. Second, any circulation cells near the top of the drying chamber are small, with the diameter of the circulation cells being less than 20% of the diameter of, the drying chamber, the circulation cells being located at least 20 cm below gas-dispersing means 24. This organized plug flow away from the top of the dryer may extend essentially to the distal end of the dryer or may extend only a portion of the way down the length of the dryer. It is generally only necessary for the downward organized plug flow to extend sufficiently far down the dryer (at least about 20 cm) such that few, if any, droplets or particles may circulate from the lower portion of the dryer back to the top of the dryer in the vicinity of gas-dispersing means 24 and atomizing means 30. Thus, organized plug flow of drying gas dramatically decreases the formation of circulation cells that entrain droplets or particles back up to the top of the drying chamber.

Two additional benefits of organized plug flow are (1) the velocity of drying gas is uniform across the entire diameter of the drying chamber, resulting in a more uniform residence time of particles in the drying chamber and improved uniformity of particle size, density and morphology, and (2) the particles generally dry more slowly, thus allowing denser, lower specific volume particles to be formed. Such low specific volume products are generally preferred as they have improved flow characteristics.

FIG. 4 illustrates one way for accomplishing the introduction of drying gas in the manner described above and that has been shown to achieve the desired organized plug flow down a portion of the drying chamber. In one embodiment, gas-dispersing means 24 consists of a plate coextensive with the interior of drying chamber 20 and bearing a multiplicity of evenly distributed perforations occupying from about 0.5 to about 5% of the surface area of the plate, preferably about 1%, with each perforation being from about 0.1 to about 6 mm in diameter, preferably from about 1.0 to about 3.0 mm. In another embodiment, the density of perforations is lower in the center of the diffuser plate, where the atomizing means extends through the plate into the drying chamber. For a cylindrical drying chamber, this lower density region extends from the center of the diffuser plate to a diameter that is about 10% to about 35% of the diameter of the drying chamber. The density of perforations in this low density region is about 10% to about 50% the density of perforations in the outer part of the diffuser plate. Gas-dispersing means 24 creates an organized plug flow of drying gas (depicted by the downward arrows in FIG. 4) and dramatically decreases large circulation cells that carry droplets and particles to the gas-dispersing means 24 and atomizing means 30. This generally greatly reduces product build-up in those two areas.

However, the spray-dryer apparatus shown in FIG. 4 generally limits the size of droplets and, in turn, product particles that may be formed without excessive build-up of material 34 on the walls of the lower portion of the drying chamber 20 and collection cone 22. One approach to avoid this problem is to adjust the atomizing conditions to produce smaller droplets and particles. A second approach is to increase the drying gas inlet temperature (and, in turn, the outlet temperature), thus inducing more rapid droplet drying. Both of these approaches, although successful, are not preferred as they lead to smaller particle sizes and/or higher particle specific volumes, both of which result in a product with poor flow characteristics. However, the inventors have found that by increasing the height of the drying chamber, i.e., the minimum distance to any surface of collection cone 22, that product can be obtained having (1) increased product yield (due to little or no build-up of material on the inner surfaces of the drying chamber or the collection cone), (2) increased particle size and (3) reduced specific volume.

Figure 5:
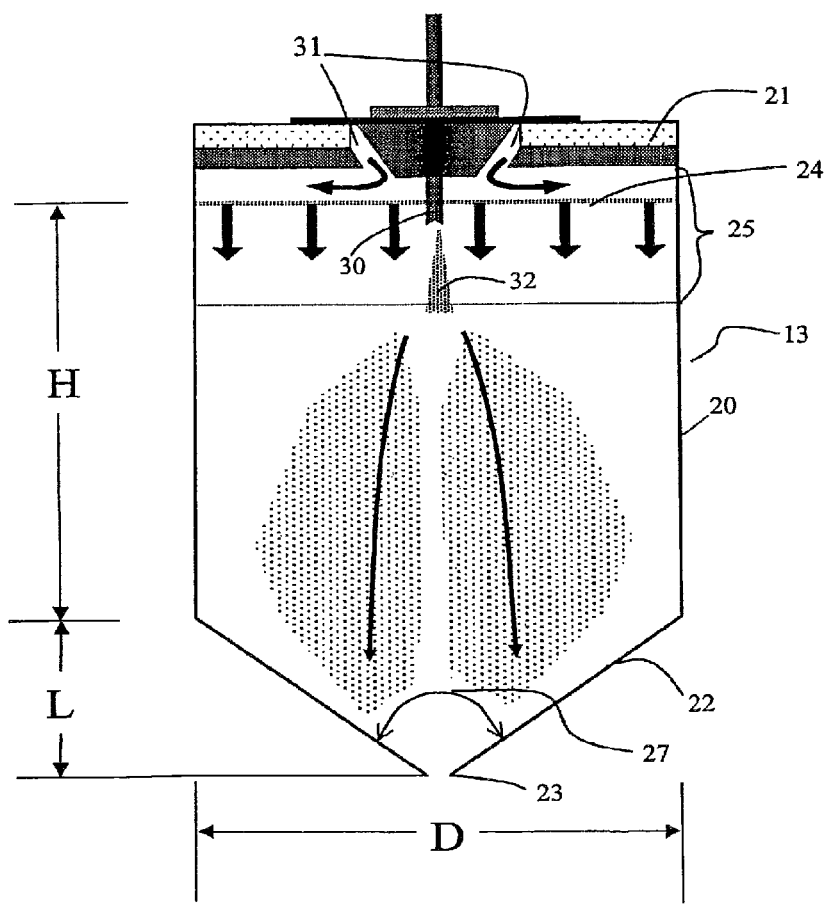
FIG. 5 is a cross-sectional schematic of the apparatus shown in FIG. 1 with both a gas-dispersing means and an extension of the drying chamber.

There is shown in FIG. 5 a cross-sectional schematic of a modified spray-drying apparatus 13 of the present invention that includes gas-dispersing means 24 of the same design as described in connection with FIG. 4. Apparatus 13 also has a drying chamber 20 having a height H that is larger than that of a conventional drying chamber. The larger height results in an increased minimum distance that a droplet travels before impinging on the walls of drying chamber 20 or of collection cone 22, allowing the droplet to dry sufficiently so that there is minimal build-up of material 34 on the inner surfaces of the drying chamber or collection cone. The larger height also allows for selection of processing conditions that result in improved properties of the product dispersion. For example, a larger height allows for longer drying times, allowing the use of atomizing means that produces larger droplets. As a result, a product dispersion with larger particles and therefore improved flow characteristics and collection efficiencies can be produced. The larger height also allows for selection of process conditions that lead to slower drying of the droplets, resulting in a product with a lower specific volume and thus improved flow characteristics. Use of the modified apparatus 13 equipped with atomizing means 30 that produces droplets with an average droplet diameter of 50 μm or larger and with less than about 10 vol % of the droplets having a size less than 10 μm, gas-dispersing means 24 that results in organized plug flow of the drying gas, and a larger height H that results in an increased minimum distance the droplets travel before impinging on the walls of drying chamber 20 or of collection cone 22, results in the formation of a homogeneous solid amorphous dispersion at high yield having large particle sizes, minimal fines, low specific volumes, high collection efficiencies, and good flow characteristics, with minimal build-up of material 34 on atomizing means 30, chamber lid 21, drying gas inlets 31, drying chamber 20 or collection cone 22.

The height H of the drying chamber 20 that provides a sufficient minimum distance the droplets travel before impinging on the walls of drying chamber 20 or of collection cone 22 is a function of several factors, including (1) the drying characteristics of the solvent-bearing feed, (2) the flow rates of solvent-bearing feed and drying gas to the spray-dryer, (3) the inlet temperature of the drying gas, (4) the droplet size and droplet size distribution and (5) the average residence time of material in the spray-dryer.

The inventors have found that even a small increase in the height of the drying chamber can result in improved performance of a spray-dryer. For example, a conventional Niro PSD-1 spray-drying apparatus designed for use with a solvent-bearing feed has a height of about 0.8 m. When a pressure nozzle is used with such a dryer, a significant fraction of the droplets are not sufficiently dry before they impinge on the wall of the drying chamber and the collection cone, resulting in build-up of material in the dryer and poor yields and poor content uniformity. However, a 1.25-fold increase in height to 1.0 m allows the droplets to become sufficiently dry so that build-up of material on the interior dryer surfaces is minimized.

The inventors have also shown that a 3.25-fold increase in the height of a conventional Niro PSD-1 spray-dryer (to 2.6 m) allows for even greater flexibility in producing homogeneous solid amorphous spray-dried dispersions with desirable properties. With such an arrangement, the spray-drying conditions can be selected that allow for formation of dispersions with large particles (i.e., greater than 50 μm), low specific volumes (i.e., less than 4 mL/gm) at high yield (i.e., greater than 95%). Dispersions with such properties cannot be produced on a conventional PSD-1 spray-dryer.

Through experimentation and finite-element modeling of the spray-drying process, the inventors have determined that for production of a homogeneous solid amorphous dispersion of a given drug and a given concentration-enhancing polymer, the height of the drying chamber should be at least 1.0 m to allow sufficient minimum distance for a droplet to travel before impinging on a surface of the drying apparatus. More preferably, the height of the drying chamber is at least 1.5 m, and most preferably at least 2.0 m. Spray-dryers that meet these minimum height requirements, combined with a gas-dispersing means that results in organized plug flow of the drying gas and a pressure nozzle, will result in the production of high-quality-product at high yield.

While the height of the drying chamber is critical to determining the minimum distance a droplet travels before impinging on a surface of the drying apparatus, the volume of the drying apparatus is also important. The capacity of a spray-dryer is determined, in part, by matching the flow rate of the solvent-bearing feed to the temperature and flow of the drying gas. Simply stated, the temperature and flow rate of the drying gas must be sufficiently high so that sufficient heat for evaporating the solvent-bearing feed is delivered to the spray-drying apparatus. Thus, as the flow rate of solvent-bearing feed is increased, the flow rate and/or temperature of the drying gas must be increased to provide sufficient energy for formation of the desired product. Since the allowable temperature of the drying gas is often limited by the chemical stability of the drug present in the solvent-bearing feed, the drying gas flow rate is often increased to allow for an increased capacity (i.e., increased flow of solvent-bearing feed) of the spray-drying apparatus. For a drying apparatus with a given volume, an increase in the drying gas flow rate will result in a decrease in the average residence time of droplets or particles in the dryer, which could lead to insufficient time for evaporation of solvent from the droplets to form a solid particle prior to impinging on a surface in the spray-dryer, even though the drying chamber has a greater height than a conventional dryer. As a result, the volume of the dryer must be sufficiently large that the droplet is sufficiently dry by the time it impinges on internal surfaces of the dryer to prevent build-up of material.

One may take into account this drying time by the "average residence time" τ, defined as the ratio of the volume of the spray-drying apparatus to the volumetric flow rate of drying gas fed to the drying apparatus, or $$\tau = \frac{V_{dryer}}{G},$$

where $V_{dryer}$ is the volume of the spray dryer and G is the volumetric flow rate of drying gas fed to the dryer. The volume of the dryer is the sum of the volumes of drying chamber 20 and collection cone 22. For a cylindrical spray-drying apparatus with a diameter D, a height H of the drying chamber, and a height L of the collection cone, the volume of the dryer $V_{dryer}$ is given as $$V_{dryer} = \frac{\pi}{4}D^2 H + \frac{\pi}{12}D^2 L$$

The inventors have determined that the average residence time should be at least 10 seconds to ensure that the droplets have sufficient time to dry prior to impinging on a surface within the spray-dryer; more preferably, the average residence time is at least 15 seconds and most preferably at least 20 seconds.

For example, for a volumetric flow of drying gas of 0.25 m³/sec and an average residence time of 20 seconds, the required volume of the spray-drying apparatus can be calculated as follows:

$$V_{dryer} = \Sigma \cdot G = 20 \text{ sec} \cdot 0.25 \text{ m}^3/\text{sec} = 5 \text{ m}^3.$$

Thus, for a spray-dryer with a volume of 5 m³, a height H of 2.3 m and a collection cone 22 with a cone angle 27 of 60° (meaning that the height L of the collection cone 22 is equal to the diameter D of the drying chamber 20 or L=D), the required diameter D of the spray-drying chamber can be calculated from the above equation, as follows:

$$\begin{aligned} V_{dryer} &= \frac{\pi}{4}D^2 H + \frac{\pi}{12}D^2 L \\ &= \frac{\pi}{4}D^2 H + \frac{\pi}{12}D^3 \\ &= 5 \\ &= \frac{\pi}{4}D^2 2.3 + \frac{\pi}{12}D^3, \end{aligned}$$

or

D=1.5 m.

Provided the diameter of the spray-dryer is at least 1.5 m, the average residence time of particles in the dryer will be at least 20 seconds, and the droplets produced by the pressure nozzle will be sufficiently dry by the time they impinge on the surface of the dryer to minimize build-up of material on the walls of the drying chamber and collection cone.

Using these criteria, the height and volume of a spray-dryer necessary to form a homogeneous solid amorphous dispersion of a drug and concentration enhancing polymer at high yield and with the desired properties can be determined.

The Drug

The present invention is useful in the formation of solid amorphous dispersions of a drug and a concentration-enhancing polymer. The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if the addition of the concentration-enhancing polymer can reduce the size of the dose needed for therapeutic efficacy or increase the rate of drug absorption in cases where a rapid onset of the drug's effectiveness is desired.

The present invention is particularly suitable for preparing a solid dispersion of and enhancing the solubility of a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. The invention finds greater utility as the solubility of the drug decreases. Thus, compositions of the present invention are preferred for low-solubility drugs having a solubility of less than 10 mg/mL, more preferred for low-solubility drugs having a solubility of less than 1 mg/mL, and even more preferred for low-solubility drugs having a solubility of less than 0.1 mg/mL. In general, it may be said that the drug has a dose-to-aqueous solubility ratio greater than 10 mL, and more typically greater than 100 mL, where the drug solubility, (mg/mL) is the minimum value observed in any physiologically relevant aqueous solution (e.g., those with pH values between 1 and 8) including USP simulated gastric and intestinal buffers, and the dose is in mg. Thus, a dose-to-aqueous-solubility ratio may be calculated by dividing the dose (in mg) by the solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein (CETP) inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific, example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—

(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; specific examples of cholesterol ester transfer protein inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester and [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

Solid Drug-Containing Dispersion

The spray-dried product formed by the method of the present invention comprise dispersions of a drug and at least one concentration-enhancing polymer. At least a major portion of the drug in the dispersion is amorphous. As used herein, the term "a major portion" of the drug means that at least 60% of the drug in the dispersion is in the amorphous form, rather than the crystalline form. By "amorphous" is meant simply that the drug is in a non-crystalline state. Preferably, the drug in the dispersion is substantially amorphous. As used herein, "substantially amorphous" means that the amount of the drug in crystalline form does not exceed about 25%. More preferably, the drug in the dispersion is "almost completely amorphous" meaning that the amount of drug in the crystalline form does not exceed about 10%. Amounts of crystalline drug may be measured by Powder X-Ray Diffraction (PXRD), Scanning Electron Microscope (SEM) analysis, differential scanning calorimetry (DSC), or any other standard quantitative measurement.

The composition formed by the inventive method may contain from about 1 to about 80 wt % drug, depending on the dose of the drug and the effectiveness of the concentration-enhancing polymer. Enhancement of aqueous drug concentrations and relative bioavailability are typically best at low drug levels, typically less than about 25 to about 40 wt %. However, due to the practical limit of the dosage form size, higher drug levels are often preferred and in many cases perform well.

The amorphous drug can exist within the solid amorphous dispersion as a pure phase, as a solid solution of drug homogeneously distributed throughout the polymer or any combination of these states or those states that lie intermediate between them. The dispersion is preferably substantially homogeneous so that the amorphous drug is dispersed as homogeneously as possible throughout the polymer. As used herein, "substantially homogeneous" means that the fraction of drug that is present in relatively pure amorphous domains within the solid dispersion is relatively small, on the order of less than 20%, and preferably less than 10% of the total amount of drug.

While the dispersion formed by the inventive method may have some drug-rich domains, it is preferred that the dispersion itself have a single glass transition temperature ($T_g$), which confirms that the dispersion is substantially homogeneous. This is in contrast to a simple physical mixture of pure amorphous drug particles and pure amorphous polymer particles which generally display two distinct $T_g$s, one being that of the drug and one that of the polymer. $T_g$ as used herein is the characteristic temperature where a glassy material, upon gradual heating, undergoes a relatively rapid (e.g., in 10 to 100 seconds) physical change from a glassy state to a rubbery state. The $T_g$ of an amorphous material such as a polymer, drug or dispersion can be measured by several techniques, including by a dynamic mechanical analyzer (DMA), a dilatometer, a dielectric analyzer, and by DSC. The exact values measured by each technique can vary somewhat, but usually fall within 10° to 30° C. of each other. Regardless of the technique used, when an amorphous dispersion exhibits a single $T_g$, this indicates that the dispersion is substantially homogenous. Dispersions formed by the method of the present invention that are substantially homogeneous generally are more physically stable and have improved concentration-enhancing properties and, in turn, improved bioavailability, relative to nonhomogeneous dispersions.

Concentration-Enhancing Polymers

Concentration-enhancing polymers suitable for use in the compositions formed by the inventive method should be inert, in the sense that they do not chemically react with the drug in an adverse manner. The polymer can be neutral or ionizable, and should have an aqueous solubility of at least 0.1 mg/mL over at least a portion of the pH range of 1-8.

The polymer is a "concentration-enhancing polymer," meaning that it meets at least one, and preferably both, of the following conditions. The first condition is that the concentration-enhancing polymer increases the maximum drug concentration (MDC) of the drug in the environment of use relative to a control composition consisting of an equivalent amount of the undispersed drug but no concentration-enhancing polymer. That is, once the composition is introduced into an environment of use, the polymer increases the aqueous concentration of drug relative to the control composition. Preferably, the polymer increases the MDC of the drug in aqueous solution by at least 1.25-fold relative to a control composition, more preferably by at least 2-fold, and most preferably by at least 3-fold. The second condition is that the concentration-enhancing polymer increases the area under the concentration versus time curve (AUC) of the drug in the environment of use relative to a control composition consisting of the drug but no polymer. (The calculation of an AUC is a well-known procedure in the pharmaceutical arts and is described, for example, in Welling, "Pharmacokinetics Processes and Mathematics," ACS Monograph 185 (1986).) More specifically, in the environment of use, the composition comprising the drug and the concentration-enhancing polymer provides an AUC for any period of from about 90 to about 270 minutes following introduction to the use environment that is at least 1.25-fold that of a control composition consisting of an equivalent quantity of drug but no polymer. Preferably, the AUC provided by the composition is at least 2-fold, more preferably at least 3-fold that of the control composition.

As used herein, a "use environment" can be either the in vivo environment of the GI tract of a mammal, particularly a human, or the in vitro environment of a test solution, such as phosphate buffered saline (PBS) solution or Model Fasted Duodenal (MFD) solution.

Concentration-enhancing polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

It is preferred that the concentration-enhancing polymer be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion-pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises non-ionizable (neutral) non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene copolymers.

A preferred class of neutral non-cellulosic polymers are comprised of vinyl copolymers of at least one hydrophilic, hydroxyl-containing repeat unit and at least one hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

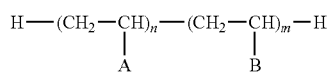

where A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular-weights from about 2,500 to about 1,000,000 daltons.

The hydrophilic, hydroxyl-containing repeat units "A" may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus, exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent "B" may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—$CH_2CH_2CH_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100 \times \left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3.

A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer polyvinylalcohol is not amphiphilic and is almost entirely water-insoluble. Preferred vinylacetate/ vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGIT® series manufactured by Rohm Tech Inc., of Malden, Mass.; amine-functionalized polyacrylates and polymethacrylates; proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGIT® series, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate-substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous-insoluble. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester-linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, ethyl carboxymethyl cellulose, cellulose acetate phthalate, carboxymethyl ethyl cellulose, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose.

Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate, cellulose acetate trimellitate and carboxymethyl ethyl cellulose. The most preferred is hydroxypropyl methyl cellulose acetate succinate (HPMCAS).

Another preferred class of polymers consists of neutralized acidic polymers. By "neutralized acidic polymer" is meant any acidic polymer in which a significant fraction of the "acidic moieties" or "acidic substituents" have been "neutralized"; that is, exist in their deprotonated form. By "neutralized acidic cellulosic polymers" is meant any cellulosic "acidic polymer" for which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram of polymer "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned U.S. Patent Application Ser. No. 60/300,255 filed Jun. 22, 2001, the relevant disclosure of which is incorporated by reference.

While specific polymers have been discussed as being suitable for use in the dispersions formable by the present invention, blends of such polymers may also be suitable. Thus, the term "concentration-enhancing polymer" is intended to include blends of polymers in addition to a single species of polymer.

The amount of concentration-enhancing polymer relative to the amount of drug present in the spray-dried dispersions formed by the present invention depends on the drug and concentration-enhancing polymer and may vary widely from a drug-to-polymer weight ratio of 0.01 to 5. However, in most cases, except when the drug dose is quite low, e.g., 25 mg or less, it is preferred that the drug-to-polymer ratio is greater than 0.05 and less than 2.5 and often the enhancement in drug concentration or relative bioavailability is observed at drug-to-polymer ratios of 1 or less or for some drugs even 0.2 or less. In cases where the drug dose is about 25 mg or less, the drug-to-polymer weight ratio may be significantly less than 0.05. In general, regardless of the dose, enhancements in drug concentration or relative bioavailability increase with decreasing drug-to-polymer weight ratio. However, due to the practical limits of keeping the total mass of a tablet, capsule or suspension low, it is often desirable to use a relatively high drug-to-polymer ratio as long as satisfactory results are obtained. The maximum drug:polymer ratio that yields satisfactory results varies from drug to drug and is best determined in the in vitro and/or in-vivo dissolution tests described below.

In general, to maximize the drug concentration or relative bioavailability of the drug, lower drug-to-polymer ratios are preferred. At low drug-to-polymer ratios, there is sufficient concentration-enhancing polymer available in solution to ensure the inhibition of the precipitation or crystallization of drug from solution and, thus, the average concentration of drug is much higher. For high drug/polymer ratios, not enough concentration-enhancing polymer may be present in solution and drug precipitation or crystallization may occur more readily. However, the amount of concentration-enhancing polymer that can be used in a dosage form is often limited by the maximum total mass of the dosage form that is acceptable. For example, when oral dosing to a human is desired, at low drug/polymer ratios the total mass of drug and polymer may be unacceptably large for delivery of the desired dose in a single tablet or capsule. Thus, it is often necessary to use drug/polymer ratios that are less than those which yield maximum drug concentration or relative bioavailability in specific dosage forms to provide a sufficient drug dose in a dosage form that is small enough to be easily delivered to a use environment.

Concentration Enhancement

The concentration-enhancing polymer is present in the spray-dried dispersions formed by the present invention in a sufficient amount so as to improve the concentration of the drug in a use environment relative to a control composition. At a minimum, the compositions formed by the present invention provide concentration-enhancement relative to a control consisting of undispersed drug alone. Thus, the concentration-enhancing polymer is present in a sufficient amount so that when the composition is administered to a use environment, the composition provides improved drug concentration relative to a control consisting of an equivalent amount of crystalline drug, but with no concentration-enhancing polymer present.

The compositions formed by the inventive method comprising the drug and concentration-enhancing polymer provide enhanced concentration of the dissolved drug in in vitro dissolution tests. It has been determined that enhanced drug concentration in in vitro dissolution tests in MFD solution or in PBS solution is a good indicator of in vivo performance and bioavailability. An appropriate PBS solution is an aqueous solution comprising 20 mM $Na_2HPO_4$, 47 mM $KH_2PO_4$, 87 mM NaCl, and 0.2 mM KCl, adjusted to pH 6.5 with NaOH. An appropriate MFD solution is the same PBS solution wherein there is also present 7.3 mM sodium taurocholic acid and 1.4 mM of 1-palmitoyl-2-oleyl-sn-glycero-3-phosphocholine. In particular, a composition formed by the inventive method can be dissolution-tested by adding it to MFD or PBS solution and agitating to promote dissolution. Generally, the amount of composition added to the test solution is that amount which, if all the drug in the composition dissolved, would produce a drug concentration that is at least about 2-fold and preferably at least about 10-fold the equilibrium solubility of the drug alone in the test solution. Higher levels of dissolved drug concentration may be demonstrated by the addition of even larger amounts of the composition.

In one aspect, the compositions formed by the inventive method provide an MDC that is at least 1.25-fold the equilibrium concentration of a control composition consisting of an equivalent quantity of drug but no polymer. In other words, if the equilibrium concentration provided by the control composition is 1 μg/mL, then a composition formed by the inventive method provides an MDC of at least about 1.25 μg/mL. The comparison composition is conventionally the undispersed drug alone (e.g. typically, the crystalline drug alone in its most thermodynamically stable crystalline form, or in cases where a crystalline form of the drug is unknown, the control may be the amorphous drug alone) or the drug plus a weight of inert diluent equivalent to the weight of polymer in the test composition. Preferably, the MDC of drug achieved with the compositions formed by the inventive method is at least about 2-fold, more preferably at least about 3-fold, the equilibrium concentration of the control composition.

Alternatively, the compositions formed by the inventive method provide in an aqueous use environment an AUC, for any period of from at least about 90 minutes to about 270 minutes following-introduction to the use environment, that is at least about 1.25-fold, preferably at least about 2-fold, and most preferably at least about 3-fold, that of a control composition consisting of an equivalent quantity of undispersed drug.

An in vitro test to evaluate enhanced drug concentration in aqueous solution can be conducted by (1) adding with agitation a sufficient quantity of control composition, typically the drug alone, to the in vitro test medium, such as an MFD or a PBS solution, to achieve equilibrium concentration of the drug; (2) adding with agitation a sufficient quantity of test composition (e.g., the drug and polymer) in the same test medium, such that if all the drug dissolved, the theoretical concentration of drug would exceed the equilibrium concentration of the drug by a factor of at least 2, and preferably by a factor of at least 10; and (3) comparing the measured MDC and/or aqueous AUC of the test composition in the test medium with the equilibrium concentration, and/or with the aqueous AUC of the control composition. In conducting such a dissolution test, the amount of test composition or control composition used is an amount such that if all of the drug dissolved the drug concentration would be at least 2-fold and preferably at least 10-fold that of the equilibrium concentration. Indeed, for some extremely insoluble drugs, in order to identify the MDC achieved it may be necessary to use an amount of test composition such that if all of the drug dissolved, the drug concentration would be 100-fold or even more, that of the equilibrium concentration of the drug.

The concentration of dissolved drug is typically measured as a function of time by sampling the test medium and plotting drug concentration in the test medium vs. time so that the MDC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid large drug particulates that would give an erroneous determination, the test solution is either filtered or centrifuged. "Dissolved drug" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources of Eatontown, N.J. under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It should be recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

Alternatively, the compositions formed by the inventive method, when dosed orally to a human or other animal, provide an AUC in drug concentration in the blood that is at least about 1.25-fold that observed when a control composition consisting of an equivalent quantity of undispersed drug is dosed. It is noted that such compositions can also be said to have a relative bioavailability of about 1.25. To facilitate dosing, a dosing vehicle may be used to administer the dose. The dosing vehicle is preferably water, but may also contain materials for suspending the test or control composition, provided these materials do not dissolve the composition or change the drug solubility in vivo. Preferably, the compositions formed by the inventive method, when dosed orally to a human or other animal, provide an AUC in drug concentration in the blood that is at least about 2-fold, more preferably at least about 3-fold, that observed when a control composition consisting of an equivalent quantity of undispersed drug is dosed. Thus, the compositions formed by the inventive method can be evaluated in either in vitro or in vivo tests, or both.

Relative bioavailability of drugs in the dispersions formed by the inventive method can be tested in vivo in animals or humans using conventional methods for making such a determination. An in vivo test, such as a crossover study, may be used to determine whether a composition of drug and concentration-enhancing polymer provides an enhanced relative bioavailability compared with a control composition consisting of a drug but no polymer as described above. In an in vivo crossover study a test composition of drug and polymer is dosed to half a group of test subjects and, after an appropriate washout period (e.g., one week) the same subjects are dosed with a control composition that consists of an equivalent quantity of drug as the test composition but with no polymer present. The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). The determination of AUC is a well-known procedure and is described, for example, in Welling, "Pharmacokinetics Processes and Mathematics," ACS Monograph 185 (1986).

Preparation of Compositions

Dispersions of the drug and concentration-enhancing polymer are made by a spray-drying process, which results in at least a major portion (at least 60%) of the drug being in the amorphous state. The dispersions generally have their maximum bioavailability and stability when the drug is dispersed in the polymer such that it is substantially amorphous and substantially homogeneously distributed throughout the polymer. In general, as the degree of homogeneity of the dispersion increases, the enhancement in the aqueous concentration of the drug and relative bioavailability increase as well. Thus, most preferred are dispersions having a single glass transition temperature, which indicates a high degree of homogeneity.

In the spray-drying process, the drug and one or more concentration-enhancing polymers are dissolved in a common solvent. "Common" here means that the solvent, which can be a mixture of compounds, will dissolve both the drug and the polymer(s). After both drug and polymer have been dissolved, the solvent is rapidly removed by evaporation in the spray-drying apparatus, resulting in the formation of a substantially homogeneous, solid amorphous dispersion. In such dispersions, the drug is dispersed as homogeneously as possible throughout the polymer and can be thought of as a solid solution of drug dispersed in the polymer(s), wherein the dispersion is thermodynamically stable, meaning that the concentration of drug in the polymer is at or below its equilibrium value, or it may be considered to be a supersaturated solid solution where the drug concentration in the dispersion polymer(s) is above its equilibrium value.

The solvent is removed by the spray-drying process. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, a portion of the heat required for evaporation of solvent may be provided by heating the spray solution.

Solvents suitable for spray-drying can be any organic compound in which the drug and polymer are mutually soluble. Preferably, the solvent is also volatile with a boiling point of 150° C. or less. In addition; the solvent should have relatively low toxicity and be removed from the dispersion to a level that is acceptable according to The International Committee on Harmonization (ICH) guidelines. Removal of solvent to this level may require a subsequent processing step such as tray-drying. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water, so long as the polymer and drug are sufficiently soluble to make the spray-drying process practicable.

The composition of the solvent-bearing feed will depend on the desired ratio of drug-to-polymer in the dispersion and the solubility of the drug and polymer in the solvent. Generally, it is desirable to use as high a combined drug and polymer concentration in the solvent-bearing feed as possible, provided the drug and polymer are dissolved in the solvent, to reduce the total amount of solvent that must be removed to form the solid amorphous dispersion. Thus, the solvent-bearing feed will generally have a combined drug and polymer concentration of at least about 0.1 wt %, preferably at least about 1 wt % and more preferably at least about 10 wt %. However, solvent-bearing feeds with lower combined drug and polymer concentrations can be used to form suitable solid-amorphous dispersions.

The solvent-bearing feed, comprising the drug and polymer, is atomized through a pressure nozzle. By "pressure nozzle" is meant an atomizer that produces droplets with an average droplet diameter of 50 µm or larger, with less than about 10 vol % of the droplets having a size less than about 10 µm. Generally, an appropriately sized and designed pressure nozzle is one that will produce droplets within this size range when the spray solution is pumped through the nozzle at the desired rate. Thus, for example, when it is desired to deliver 400 g/min of a spray solution to a PSD-1 dryer, a nozzle must be chosen that is matched to the viscosity and flow rate of the solution to achieve the desired average droplet size. Too large a nozzle will deliver too large a droplet size when operated at the desired flow rate. This is particularly true the higher the viscosity of the spray solution. Droplets that are too large result in the rate of drying being too slow, which can yield nonhomogeneous dispersions. Use of a nozzle that is too small can yield droplets that are undesirably small or require an unacceptably high pump pressure to achieve the desired flow rate, particularly for high viscosity feed solutions.

A vast majority of atomizers atomize the liquid feed into droplets with a distribution of sizes. The size distribution of droplets produced by an atomizer can be measured by several techniques, including mechanical techniques, such as the molten-wax and frozen-drop techniques; electrical techniques, such as charged-wire and hot-wire techniques; and optical techniques, such as photography and light-scattering techniques. One of the more common methods for determining the droplet size distribution produced by an atomizing means is through the use of a Malvern Particle Size Analyzer, available from Malvern Instruments Ltd. of Framingham, Mass. Further details about the principles used to determine droplet size and droplet size distribution using such instruments can be found in Lefebvre, *Atomization and Sprays* (1989).

The data obtained using a droplet-size analyzer can be used to determine several characteristic diameters of the droplets. One of these is $D_{10}$, the drop diameter corresponding to the diameter of droplets that make up 10% of the total liquid volume containing droplets of equal or smaller diameter. In other words, if $D_{10}$ is equal to 10 µm, 10 vol % of the droplets have a diameter less than or equal to 10 µm. Thus, it is preferred that the atomizing means produces droplets such that $D_{10}$ is greater than about 10 µm, meaning that 90 vol % of the droplets have a diameter of greater than about 10 µm. This requirement ensures the number of fines in the solidified product (i.e., particles with diameters of less than 10 µm) is minimized. Preferably, $D_{10}$ is greater than about 15 µm, more preferably greater than about 20 µm.

Another useful characteristic diameter of the droplets produced by an atomizer is $D_{90}$, the droplet diameter corresponding to the diameter of droplets that make up 90% of the total liquid volume containing droplets of equal or smaller diameter. In other words, if $D_{90}$ is equal to 100 µm, 90 vol % of the droplets have a diameter less than or equal to 100 µm. For producing substantially homogeneous, substantially amorphous dispersions using the technology of the present invention, the inventors have found that $D_{90}$ should be less than about 300 µm, preferably less than 250 µm. If $D_{90}$ is too high, the rate of drying of the larger droplets may be too slow, which can yield nonhomogeneous dispersions.

Another useful parameter is the "Span," defined as $$\text{Span} = \frac{D_{90} - D_{10}}{D_{50}},$$

where $D_{50}$ is the diameter corresponding to the diameter of droplets that make up 50% of the total liquid volume containing droplets of equal or smaller diameter, and $D_{90}$ and $D_{10}$ are defined as above. Span, sometimes referred to in the art as the Relative Span Factor or RSF, is a dimensionless parameter indicative of the uniformity of the drop size distribution. Generally, the lower the Span, the more narrow the droplet size distribution produced by the atomizing means. A narrower droplet size distribution generally leads to a narrower particle size distribution for the dried particles, resulting in improved flow characteristics. Preferably, the Span of the droplets produced by the present invention is less than about 3, more preferably less than about 2, and most preferably less than about 1.5.

The size of the solid dispersion particles formed in the spray-dryer are generally somewhat smaller than the size of the droplets produced by the atomizing means. Typically, the characteristic diameter of the dispersion particles is about 80% the characteristic diameter of the droplets. Thus, in one aspect, the process of the present invention produces a solid amorphous dispersion with an average diameter of about 40 µm or larger, with less than about 10 vol % of the particles having a size less than about 8 µm. Preferably, at least 80 vol % of the dispersion particles, and more preferably at least 90 vol % have diameters larger than 10 µm. The particles may have a bulk specific volume of less than 5 mL/g, and preferably less than 4 mL/g. The particles may have an average particle size of at least 40 µm, preferably at least 50 µm.

When selecting an atomizer for use in forming a homogeneous solid amorphous dispersion, several factors should be considered, including the desired flow rate, the maximum allowable liquid pressure, and the viscosity and surface tension of the solvent-bearing feed. The relationship between these factors and their influence on droplet-size and droplet size distribution are well-known in the art.

As noted above, the selection of an atomizer will depend upon the scale of the spray-drying apparatus used. For smaller scale apparatus, examples of suitable atomizers include the SK and TX spray dry nozzle series from Spraying Systems, Inc. of Wheaton, Ill.; the WG series from Delavan-LTV of Widnes, Cheshire, England; and the Model 121 nozzle from Dusen Schlick GMBH of Untersiemau, Germany. For larger scale apparatus, exemplary atomizers include the SDX and SDX III nozzles from Delavan LTV.

In many cases the solvent-bearing feed is delivered to the atomizer under pressure. The liquid pressure required is determined by the design of the pressure nozzle, the size of the nozzle orifice, the viscosity and other characteristics of the solvent-bearing feed, and the desired droplet size and size distribution. Generally, liquid pressures should range from 2 to 200 atm or more, with 4 to 150 atm being more typical.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous dispersion instead of separating into drug-rich and polymer-rich phases. As noted above, to get large enhancements in concentration and bioavailability it is often necessary to obtain as homogeneous a dispersion as possible.

As noted above, the average residence time of particles in the drying chamber should be at least 10 seconds, preferably at least 20 seconds. However, the actual time the powder remains in the drying chamber is typically longer than the minimum drying time, as calculated above. Typically, following solidification, the powder formed stays in the spray-drying chamber for about 5 to 60 seconds, causing further evaporation of solvent. The final solvent content of the solid dispersion as it exits the dryer should be low, since this reduces the mobility of drug molecules in the dispersion, thereby improving its stability. Generally, the solvent content of the dispersion as it leaves the spray-drying chamber should be less than about 10 wt %, preferably less than about 3 wt % and most preferably less than about 1 wt %. A subsequent processing step, such as tray-drying, may be used to remove the solvent to this level.

Excipients and Dosage Forms

Although the key ingredients present in the solid amorphous dispersion are simply the drug and the concentration-enhancing polymer, other excipients may be included in the dispersion to improve performance, handling, or processing of the dispersion. Optionally, once formed, the dispersion may be mixed with other excipients in order to formulate the composition into tablets, capsules, suppositories, suspensions, powders for suspension, creams, transdermal patches, depots, and the like. The dispersion may be added to other dosage form ingredients in essentially any manner that does not substantially alter the drug. The excipients may be either separate from the dispersion and/or included within the dispersion.

Generally, excipients such as surfactants, pH modifiers, fillers, matrix materials, complexing agents, solubilizers, pigments, lubricants, glidants, flavorants, and so forth may be used for customary purposes and in typical amounts without adversely affecting the properties of the compositions. See for example, *Remington's Pharmaceutical Sciences* (18th ed. 1990).

One very useful class of excipients is surfactants, preferably present from 0 to 10 wt %. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate (DOCUSATE SODIUM, available from Mallinckrodt Spec. Chem., St. Louis, Mo.); polyoxyethylene sorbitan fatty acid esters (TWEEN®, available from ICI Americas Inc., Wilmington, Del.; LIPOSORB® O-20, available from Lipochem Inc., Patterson N.J.; CAPMUL® POE-0, available from Abitec Corp., Janesville, Wis.); and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by, for example, facilitating wetting, or otherwise increase the rate of drug release from the dosage form.

The addition of pH modifiers such as acids, bases, or buffers may be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is cationic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, dibasic calcium phosphate (anhydrous and dihydrate) and starch.

Examples of disintegrants include sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE (available from BASF Corporation).

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending-agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include silicon oxide and lactose.

Examples of solubilizers include ethanol, propylene glycol or polyethylene glycol.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions.

Compositions of the present invention may be delivered by a wide variety of routes, including, but not limited to, oral, nasal, rectal, vaginal, subcutaneous, intravenous, and pulmonary. Generally, the oral route is preferred.

Compositions of the invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

Compositions of the invention may be formulated in various forms so that they are delivered as a suspension of particles in a liquid vehicle. Such suspensions may be formulated as a liquid or as a paste at the time of manufacture, or they may be formulated as a dry powder with a liquid, typically water, added at a later time but prior to oral administration. Such powders that are constituted into a suspension are often referred to as sachets or oral powders for constitution (OPC). Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Compositions of the present invention may be used to treat any condition that is subject to treatment by administering a drug.

Example 1

A solid amorphous dispersion was prepared using a spray-drying apparatus of substantially the same configuration as that shown in FIG. 5. The dispersion comprised 25 wt % of the low-solubility drug 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 1") and 75 wt % of the amphiphilic polymer hydroxypropyl methyl cellulose acetate succinate (HPMCAS). Drug 1 was mixed in a solvent (acetone) together with a "medium fine" grade (AQUOT-MF) of HPMCAS (manufactured by Shin Etsu) to form a spray solution. The spray solution comprised 2.5 wt % Drug 1, 7.5 wt % HPMCAS, and 90 wt % acetone. The spray solution was pumped using a high pressure pump (Z-Drive 2000 High Pressure Gear Pump from Zenith, Inc. of Sanford, N.C.) to a spray-dryer (Niro type XP Portable Spray-Dryer with a Liquid Feed Process Vessel Model No. PSD-1) equipped with a pressure nozzle (Spraying Systems Pressure Nozzle and Body, Model No. SK 71-16). The droplet size produced by this pressure nozzle was determined using a Malvern Particle Size Analyzer with the following results: the mean droplet diameter was 125 μm, $D_{10}$ was 64 μm, $D_{50}$ was 110 μm and $D_{90}$ was 206 μm, resulting in a Span of 1.3.

The spray-dryer was modified such that the height of the drying chamber was larger than that supplied with a standard PSD-1 dryer. The dimensions of the spray-dryer were as follows:
D=0.8 m
H=1.0 m
L=0.8 m.
Thus, the volume of the spray-drying apparatus was $$V_{dryer} = \frac{\pi}{4}D^2H + \frac{\pi}{12}D^2L$$

$$= \frac{\pi}{4} \cdot (0.8 \text{ m})^2 \cdot (1.0 \text{ m}) + \frac{\pi}{12}(0.8 \text{ m})^2(0.8 \text{ m})$$

$$= 0.65 \text{ m}^3.$$

The spray-dryer was also equipped with a gas-disperser to produce organized plug flow of drying gas there-through. The gas-disperser consisted of a stainless steel plate with a diameter of 0.8 m that extended across the top of the drying chamber. The plate had a multiplicity of 1/16-inch (1.7 mm) perforations occupying about 1% of the surface area of the plate. The perforations were uniformly distributed across the plate, except that the density of perforations at the center 0.2 m of the gas-disperser plate was about 25% of the density of perforations in the outer part of the plate. The use of the diffuser plate resulted in organized plug flow of drying gas through the drying chamber and dramatically decreased product recirculation within the spray-dryer. The pressure nozzle sat flush with the gas-disperser plate during operation.

The spray solution was pumped to the spray-dryer at 180 g/min at a pressure of 19 atm (262 psig). Drying gas (nitrogen) was delivered to the gas-disperser plate at an inlet temperature of 103° C. and a flow rate of 1.6 standard m³/min. The evaporated solvent and drying gas exited the spray drier at a temperature of 51±4° C.

The minimum residence time for the droplets in the spray drier was calculated as $$\tau = \frac{0.65}{1.6} = 0.41 \text{ min} \times \frac{60 \text{ sec}}{\text{min}} = 24 \text{ sec}.$$

The spray-dried dispersion formed by this process was collected in a cyclone and then dried in a solvent tray dryer by spreading the spray-dried particles onto polyethylene-lined trays to a depth of not more than 1 cm and then drying them at 40° C. for 16 hours. After drying, the solid dispersion of Example 1 contained 25 wt % Drug 1. Table 1 summarizes the spray-drying conditions used. The overall yield for this process was 96%. Inspection of the spray drier after formation of the dispersion showed no evidence of product build-up on the spray-dryer top, the pressure nozzle, the walls of the drying chamber, or on the chamber cone.

Control 1 (C1) consisted of a solid amorphous dispersion of Drug 1 with HPMCAS-MF, spray-dried using a two-fluid spray nozzle (cocurrent, external mix, with a 1.0 mm liquid orifice, Niro Model No. 15698-0100) using the same apparatus. The spray-drying conditions are summarized in Table 1.

TABLE 1

| Ex. No. | Drug Mass (g) | Polymer Mass (g) | Solvent Mass (g) | Nozzle | Nozzle Pressure (psig/atm) | Feed Rate (g/min) | $T_{in}$ (° C.) | $T_{out}$ (° C.) | Yield (%) |
|---|---|---|---|---|---|---|---|---|---|
| 1 | 138 | 416 | 4990.5 | SK 79-16 | 262/19 | 180 | 103 | 51 | 96 |
| C1 | 24 | 72 | 855 | Niro 2-fluid | 42/4 | 190 | 135 | 50 | 85 |

Samples of Example 1 were analyzed by various methods to determine the physical properties of the dispersion. First, powder X-ray diffraction analysis was performed on Example 1 using an AXS D8 Advance from Bruker, Inc. of Madison, Wis. This analysis showed no crystalline peaks in the diffractogram, indicating that the drug in the dispersion was almost completely amorphous.

The concentration enhancement provided by the dispersion of Example 1 was demonstrated in a dissolution test. For this test, samples containing 7.2 mg of Example 1 were added to microcentrifuge tubes, in duplicate. The tubes were placed in a 37° C. temperature-controlled chamber, and 1.8 mL PBS at pH 6.5 and 290 mOsm/kg was added. The samples were quickly mixed using a vortex mixer for about 60 seconds. The samples were centrifuged at 13,000 G at 37° C. for 1 minute. The resulting supernatant solutions were then sampled and diluted 1:6 (by volume) with methanol and then analyzed by high-performance liquid chromatography (HPLC) at a UV absorbance of 256 nm using a Waters Symmetry C8 column and a mobile phase consisting of 15% (0.2% H3PO4)/85% methanol. The contents of the tubes were mixed on the vortex mixer and allowed to stand undisturbed at 37° C. until the next sample was taken. Collections of the samples were made at 4, 10, 20, 40, 90, and 1200 minutes. Control 1 and crystalline Drug 1 were tested using the same procedure. The results are shown in Table 2.

TABLE 2

| Sample | Time (min) | Drug 1 Concentration (μg/ml) | AUC (min-μg/ml) |
|---|---|---|---|
| Example 1 | 0 | 0 | 0 |
| (spray-dried using | 4 | 259 | 500 |
| pressure nozzle) | 10 | 671 | 3,300 |
| | 20 | 704 | 10,200 |
| | 40 | 717 | 24,400 |
| | 90 | 666 | 59,000 |
| | 1200 | 161 | 518,000 |
| Control C1 | 0 | 0 | 0 |
| (spray-dried using | 4 | 223 | 400 |
| two-fluid nozzle) | 10 | 513 | 2,600 |
| | 20 | 657 | 8,500 |
| | 40 | 675 | 21,800 |
| | 90 | 711 | 56,500 |
| | 1200 | 387 | 665,900 |
| Crystalline Drug 1 | 0 | 0 | 0 |
| | 4 | <1 | <2 |
| | 10 | <1 | <8 |
| | 20 | <1 | <18 |
| | 40 | <1 | <38 |
| | 90 | <1 | <88 |
| | 1200 | <1 | <1,200 |

The concentrations of drug obtained in these samples were used to determine the values of the maximum concentration of drug in the first ninety minutes ($C_{max90}$) and the area under the curve of drug concentration versus time in the first ninety minutes ($AUC_{90}$). The results are shown in Table 3. These data show that the dispersion of Example 1 provided a $C_{max90}$ that was greater than 717-fold that of the crystalline control, while the $AUC_{90}$ was greater than 670-fold that of the crystalline control. The data also show that the dispersion of Example 1, made using the pressure nozzle, provided about the same concentration enhancement as that of the dispersion of Control 1 made using a two-fluid nozzle.

TABLE 3

| Sample | $C_{max90}$ (μg/mL) | $AUC_{90}$ (min*μg/mL) |
|---|---|---|
| Example 1 | 717 | 59,000 |
| Control C1 | 711 | 56,500 |
| Crystalline Drug 1 | <1 | <88 |

Figure 6:
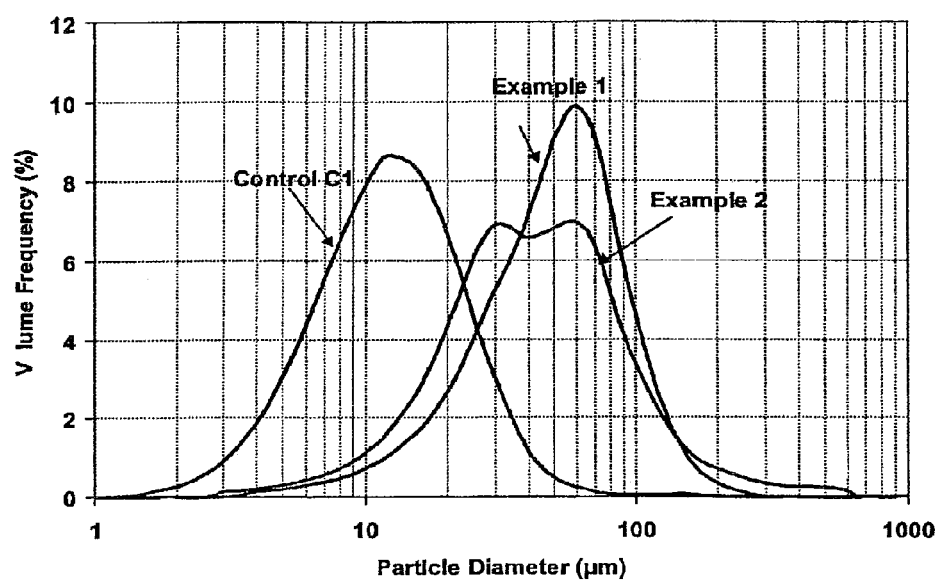
FIGS. 6-7 are graphs showing a comparison of median particle sizes and particle size distributions of spray-dried drug dispersions made using a conventional spray-drying apparatus and using an apparatus of the present invention.

The particle size distribution of the dispersions of Example 11 and Control C1 were determined by light scattering analysis of each dry solid dispersion using an LA-910 Model light-scattering particle size analyzer from Horiba, Inc. of Irvine, Calif. FIG. 6 shows volume frequency (%) versus particle diameter (μm) for Example 1 and Control C1. From these data, the mean particle diameter (the peak of the volume frequency curve) and the percent fines (area under the volume frequency curve at particle size less than about 10 μm divided by the total area under the curve) are summarized in Table 4. These data show that the mean diameter of the dispersion particles formed using a pressure nozzle and the spray-dryer design of FIG. 5 (Example 1) were larger than the mean diameter of the dispersion particles formed by the same spray-dryer using a two-fluid nozzle (Control C1). In addition, the number of fines in the dispersion of Example 1 was greatly reduced.

TABLE 4

| Sample | Mean Particle Diameter (μm) | Particles Having a Diameter of Less than 10 μm (%) |
|---|---|---|
| Example 1 | 53 | 2.9 |
| Control C1 | 15 | 42 |

The bulk and tapped specific volume of the dispersion of Example 1 was determined using the following procedure. A sample of the dispersion of Example 1 was poured into a 100-mL graduated cylinder, the tare weight of which had been measured, and the volume and weight of the sample recorded. The volume divided by the weight yielded the bulk specific volume of 4.8 mL/g. Next, the cylinder containing the dispersion was tapped 1000 times using a VanKel tap density instrument, Model 50-1200. The tapped volume divided by the same weight of dispersion yielded a tapped specific volume of 3.1 mL/g. Similar tests were performed with the dispersion of Control C1. The results, reported in Table 5, indicate that the dispersion made with the pressure nozzle (Example 1) had a lower specific volume (both bulk and tapped) than the dispersion made using a two-fluid nozzle (Control C1). Lower specific volume results in improved flow characteristics for the dispersion.

TABLE 5

| Sample | Bulk Specific Volume (mL/g) | Tapped Specific Volume (mL/g) |
|---|---|---|
| Example 1 | 4.8 | 3.1 |
| Control C1 | 5.7 | 3.3 |

Comparative Example 1

A solid amorphous dispersion of the same composition as that of Example 1 is made using a spray-drying apparatus of substantially the same configuration as that shown in FIG. 4, with a gas-disperser plate of the same configuration as in Example 1 and having the following dimensions:

D=0.8 m
H=0.8 m
L=0.8 m.

The volume of the spray-drying apparatus is calculated to be 0.53 $m^3$.

When such a spray-dryer is operated under the same conditions as in Example 1, build-up of material on the walls of the drying chamber and collection cone is predicted, resulting in poor content uniformity and poor yield.

Example 2

A solid amorphous dispersion was prepared as in Example 1 with the same spray-dryer configuration as in Example 1, except that the height of the drying chamber H was 2.3 m, resulting in a larger volume for the drying chamber. Thus, the volume of the spray-drying apparatus was 1.29 $m^3$. Table 6 gives the spray-drying conditions used. Nitrogen drying gas was circulated through the gas-disperser plate at an inlet temperature of 45° C. and a flow rate of 1.4 standard $m^3$/min. The evaporated solvent and wet drying gas exited the spray-dryer at a temperature of 10° C.

Referring to Equation I above, the minimum residence time for the droplets in the spray drier was calculated as $$\tau = \frac{1.29}{1.4} = 0.92 \text{ min} \times \frac{60 \text{ sec}}{\text{min}} = 55 \text{ sec.}$$

TABLE 6

| Drug Mass (g) | Polymer Mass (g) | Solvent Mass (g) | Nozzle | Nozzle Pressure (psig/atm) | Feed Rate (g/min) | $T_{in}$ (° C.) | $T_{out}$ (° C.) | Yield (%) |
|---|---|---|---|---|---|---|---|---|
| 150 | 450 | 5400 | SK 80-16 | 290/21 | 206 | 45 | 10 | 88 |

Inspection of the spray-dryer after formation of the dispersion showed no evidence of product build up on the spray-dryer top, the pressure nozzle, the walls of the drying chamber, or on the chamber cone.

The physical properties of the dispersions of Example 2 were determined as in Example 1. The results are summarized in Table 7, which also includes the results for Example 1, Control C1, and the crystalline Drug 1.

TABLE 7

| Sample | $C_{max90}$ (µg/mL) | $AUC_{90}$ (min*µg/mL) | Mean Particle Diameter (µm) | Particles Having a Diameter of Less Than 10 µm (%) | Bulk Specific Volume (mL/g) | Tapped Specific Volume (mL/g) |
|---|---|---|---|---|---|---|
| Example 1 | 717 | 59,000 | 70 | 2.4 | 4.8 | 3.1 |
| Example 2 | 710 | 55,100 | 39 | 4.6 | 3.6 | 2.3 |
| Control C1 | 711 | 56,500 | 20 | 17 | 5.7 | 3.3 |
| Crystalline Drug 1 | <1 | <88 | — | — | — | — |

The results show that the dispersion made with the larger volume spray-dryer of Example 2 had similar dissolution properties as the dispersions of Example 1 and Control C1, providing a $C_{max90}$ value that was greater than 720-fold that of crystalline Drug 1 alone, and an $AUC_{90}$ value that was greater than 626-fold that of crystalline Drug 1 alone. Furthermore, the mean particle size of the dispersion of Example 2 was larger than the dispersion-made using the 2-fluid nozzle (Control C1), and there were significantly fewer fines in the dispersion of Example 2. The use of the larger volume spray-dryer in Example 2 also resulted in a product with a lower specific volume, which yielded improved flow characteristics.

Example 3

A solid amorphous dispersion comprising 50 wt % of the low solubility drug 5-chloro-1H-indole-2-carboxylic acid [(1S)-benzyl-(2R)-hydroxy-3-((3R,4S)-dihydroxy-pyrrolidin-1-yl-)-3-oxypropyl]amide ("Drug 2") with HPMCAS-MF was made using the spray-drying apparatus of Example 1 using a solvent comprising a mixture of 10 wt % water in acetone. The spray-drying conditions are given in Table 8. Nitrogen drying gas was delivered to the gas-disperser plate at an inlet temperature of 103° C. and a flow rate of 1.6 standard m³/min. The evaporated solvent and drying gas exited the spray drier at a temperature of 51±4° C.

Referring to Equation I above, the minimum residence time for the droplets in the spray drier was calculated as $$\tau = \frac{0.65}{1.6} = 0.41 \text{ min} \times \frac{60 \text{ sec}}{\text{min}} = 24 \text{ sec.}$$

Inspection of the spray-dryer after formation of the dispersion showed no evidence of product build-up on the spray-dryer top, the pressure nozzle, the walls of the drying chamber or on the chamber cone.

Control 2 (C2) consisted of a dispersion of Drug 2 with HPMCAS-MF, spray-dried using a Niro two-fluid external-mix spray nozzle using the same apparatus as in Example 1. Control C2 contained 50 wt % Drug 2. The spray conditions are noted in Table 8.

TABLE 8

| Ex. No. | Drug Mass (g) | Polymer Mass (g) | Solvent Mass (g) | Nozzle | Nozzle Pressure (psig/atm) | Feed Rate (g/min) | $T_{in}$ (° C.) | $T_{out}$ (° C.) | Yield (%) |
|---|---|---|---|---|---|---|---|---|---|
| 3 | 200 | 200 | 2263 | SK 80-16 | 145/11 | 165 | 110 | 44 | 96 |
| C2 | 250 | 250 | 2831 | Niro 2-fluid | 39/4 | 39 | 113 | 43 | 85 |

The physical properties of the dispersions of Example 3, Control C2 and crystalline Drug 2 alone were determined as Example 1 with the following exceptions. For concentration enhancement, sufficient quantities of the dispersion were added to the microcentrifuge tubes such that the concentration obtained if all of the drug had dissolved was 2000 µg/mL. Samples were analyzed by HPLC, with absorbance at 297 nm (Hewlett Packard 1100 HPLC, Zorbax SB C18 column, 35% acetonitrile/65% $H_2O$).

Figure 7:
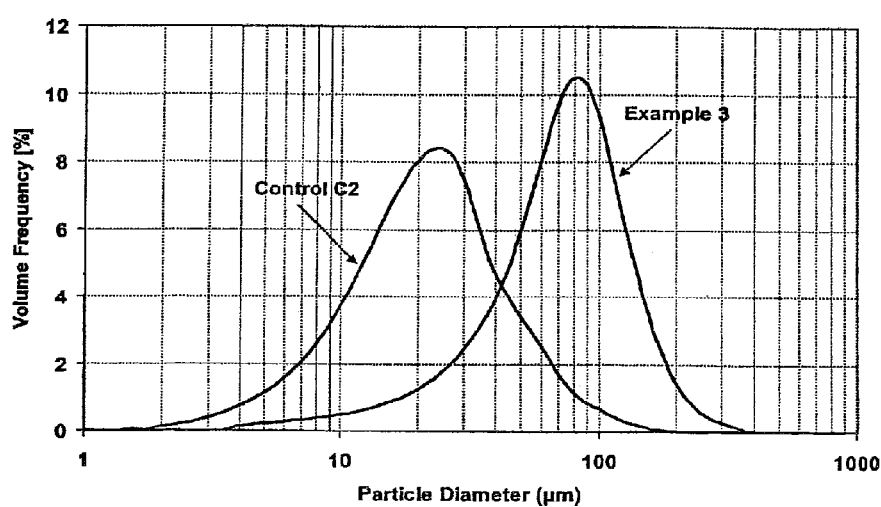

The results of these physical property tests are summarized in Table 9 and show that the dispersion made using the pressure nozzle and the spray-dryer design of FIG. 5 (Example 3) had a larger mean particle diameter and fewer fines than the dispersion made using the same dryer design with a two-fluid nozzle (Control C2). FIG. 7 shows volume frequency versus particle diameter for Example 3 (made with a pressure nozzle) and for Control C2. The dissolution performance of the dispersion of Example 3 was slightly better than that of the dispersion made using a two-fluid nozzle. The dispersion of Example 3 provided a $C_{max90}$ that was 4.9-fold that of the crystalline control, and an AUC$_{90}$ that was 4.1-fold that of the crystalline control. Finally, the Example 3 dispersion had a lower specific volume than that of Control C2, yielding a product with improved flow characteristics.

TABLE 9

| Sample | C$_{max90}$ (μg/mL) | AUC$_{90}$ (min*μg/mL) | Mean Particle Diameter (μm) | Particles Having a Diameter of Less Than 10 μm (%) | Bulk Specific Volume (mL/g) | Tapped Specific Volume (mL/g) |
|---|---|---|---|---|---|---|
| Example 3 | 730 | 52,200 | 70 | 2.4 | 4.2 | 3.0 |
| Control C2 | 580 | 49,600 | 20 | 17 | 5.0 | 3.2 |
| Crystalline Drug 2 | 149 | 12,800 | — | — | — | — |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A process for producing a pharmaceutical composition comprising the steps:
    (a) forming a feed solution comprising a drug, a polymer and a solvent, wherein said polymer is selected from the group consisting of hydroxypropyl methyl cellulose, hydroxypropyl cellulose, carboxymethyl ethyl cellulose, hydroxypropyl methyl cellulose acetate succinate, hydroxypropyl methyl cellulose phthalate, cellulose acetate phthalate, cellulose acetate trimellitate, vinyl polymers and copolymers having at least one substituent selected from the group consisting of hydroxyl, alkylacyloxy, and cyclicamido, and polyvinyl alcohols that have at least a portion of their repeat units in hydrolyzed form, polyvinyl pyrrolidone, poloxamers, and blends thereof;
    (b) directing said feed solution to a spray-drying apparatus comprising
        (i) a drying chamber having a volume V$_{dryer}$ and a height H,
        (ii) atomizing means for atomizing said feed solution into droplets, and
        (iii) a source of heated drying gas for drying said droplets, said source delivering said drying gas to said drying chamber at a flow rate of G,
    wherein V$_{dryer}$ is measured in m$^3$,
    H is at least 1.0 m,
    G is measured in m$^3$/sec,
    and wherein the following mathematical relationship is satisfied $$\frac{V_{dryer}}{G} \geq 10 \text{ seconds};$$

(c) atomizing said feed solution into droplets in said drying chamber by said atomizing means;
    (d) contacting said droplets with said heated drying gas to form particulates of a solid amorphous dispersion of said drug homogeneously distributed throughout said polymer; and
    (e) collecting said particulates.

2. The process of claim 1 wherein said droplets have an average diameter of at least 50 μm and a D$_{10}$ of at least 10 μm.

3. The process of claim 1 wherein at least 80 vol % of said particulates have diameters of greater than 10 μm.

4. The process of claim 1 wherein at least 90 vol % of said particulates have diameters of greater than 10 μm.

5. The process of claim 1 wherein said particles have an average diameter of at least 40 μm.

6. The process of claim 1 wherein said particles have an average diameter of at least 50 μm.

7. The process of claim 1 wherein said spray-drying apparatus further comprises a gas disperser for dispersing said gas into said drying chamber.

8. The process of claim 7 wherein said drying gas is dispersed into said drying chamber such that the primary axis of flow of said drying gas is parallel to the axis of said atomizing means.

* * * * *